US005650846A

United States Patent [19]
Yin et al.

[11] Patent Number: 5,650,846
[45] Date of Patent: Jul. 22, 1997

[54] MICROCOLUMNAR ANALYTICAL SYSTEM WITH OPTICAL FIBER SENSOR

[75] Inventors: Hongfeng Yin, Cupertino; Catherine Keely Templin, Los Altos, both of Calif.

[73] Assignee: Hewlett-Packard Company, Palo Alto, Calif.

[21] Appl. No.: 562,082

[22] Filed: Nov. 21, 1995

[51] Int. Cl.$^6$ .................... G01N 21/64; G01N 21/05
[52] U.S. Cl. .................. 356/318; 250/458.1; 250/459.1; 356/410
[58] Field of Search .................. 356/410, 440, 356/246, 318; 250/458.1, 459.1

[56] References Cited

U.S. PATENT DOCUMENTS

| | | | |
|---|---|---|---|
| 4,675,300 | 6/1987 | Zare et al. | 436/172 |
| 5,006,210 | 4/1991 | Yeung et al. | 204/180.1 |
| 5,021,646 | 6/1991 | Weinberger et al. | 250/277.11 |
| 5,114,551 | 5/1992 | Hjerten et al. | 204/180.1 |
| 5,324,401 | 6/1994 | Yeung et al. | 204/180.1 |

FOREIGN PATENT DOCUMENTS 60-36936  2/1985  Japan ..................... 356/246

Primary Examiner—Vincent P. McGraw

[57] ABSTRACT

An analytical system for analyzing a fluid sample is disclosed. The analytical system includes a microcolumn for conducting the fluid sample, a light source for delivering light through the microcolumnar wall into the microcolumn near the outlet end of that microcolumn, and an optical fiber aligned with the microcolumn to detect light that radiates from the fluid sample without passing through the microcolumnar wall. The microcolumn has an inlet end and an outlet end. A light-inlet end of the optical fiber is nonfixedly coupled to the outlet end of the microcolumn. As the fluid sample is driven from the inlet end to the outlet end of the microcolumn, a light of a suitable wavelength is directed at the microcolumn near its outlet end to cause light interaction with the fluid sample. As a result, light radiates from the fluid sample. This light is collected by the optical fiber to provide information on the presence or quantity of an analyte in the fluid sample.

20 Claims, 7 Drawing Sheets

MICROCOLUMNAR ANALYTICAL SYSTEM WITH OPTICAL FIBER SENSOR

FIELD OF THE INVENTION

The present invention relates to an analytical apparatus with a microcolumn and the detection of changes in light interaction with a fluid sample being analyzed in the apparatus. More particularly, the present invention relates to an analytical apparatus having a microcolumn interfaced with fiber optics.

BACKGROUND

Recently, analytical techniques that employ small tubular structures (i.e., microcolumns) have gained wide acceptance. For example, capillary electrophoresis (CE) and liquid chromatography (LC), such as high performance liquid chromatography (HPLC), are commonly used techniques for separating analytes, including macromolecules and biomolecules such as proteins, nucleic acids, DNA molecules and fragments, carbohydrates, fatty acids, peptides, and the like. In these techniques, a sample that is suspected of containing analytes is sent through a microcolumn. As the molecules in the sample migrate through the microcolumn, depending on the interaction of the analytes with the other substances (such as packing material) in the microcolumn, the analytes separate from one another.

A very useful technique for detecting analytes passing through a microcolumn (such as the aforementioned) involves directing an incident light to the analytes and detecting the light interaction that results. For example, U.S. Pat. No. 4,675,300 (Zare et al.) describes an electrokinetic process and an apparatus employing coherent radiation-excited fluorescence for detecting analytes. In this system, apparently, laser light is directed at an angle to a translucent section of a capillary to irradiate a sample. The resulting fluorescence light passes through the capillary and is detected by an optical fiber positioned at an angle to the capillary.

U.S. Pat. No. 5,006,210 (Yeung et al.) also describes an analytical system that uses light interaction. Here, analytes in capillary zone electrophoresis are detected by laser-induced indirect fluorescence detection. The laser light is directed at an angle to the capillary and the fluorescence light is also detected by a detector pointing at an angle to the capillary.

U.S. Pat. No. 5,324,401 (Yeung et al.) describes a fluorescence detection system for capillary electrophoresis. This detection system can simultaneously excite fluorescence and substantially simultaneously monitor analyte separation in multiple capillaries. The system has an array of capillaries, each of which has an optical fiber inserted into its outflow end to excite the sample therein. The resulting fluorescence light passes through the capillary walls and is imaged by a CCD camera viewing perpendicularly relative to the axis of the capillary.

In the excitation of a sample and in the detection of light from the light interaction, to increase the signal to noise ratio, it is preferred that more of the excitation light from a light source impinges on the sample and more of the resultant out-going (e.g., fluorescence) light from the sample be collected for detection. In the prior art, as described in the aforementioned patents, the detector is typically directed at an acute or right angle to a detection zone of the capillary in air. In addition, often the excitation light source is also directed at an acute angle to the capillary. The present invention affords a more compact construction and better signal collection than the prior art systems.

SUMMARY

The present invention provides an analytical apparatus for analyzing a fluid sample. The analytical apparatus includes a system for causing a light interaction with the fluid sample and detecting such a light interaction (i.e., the system collects optical signals from the fluid sample). The system includes a microcolumn for conducting the fluid sample (in some cases also separating analytes in the fluid sample), a light source for delivering light through the microcolumnar wall into the microcolumn proximate the outlet end of that microcolumn, and an optical fiber aligned with the microcolumn to detect light that radiates from the fluid sample (e.g., fluorescence from an analyte in the fluid sample). The microcolumn has a longitudinal axis and a microcolumnar wall. Light radiated from the fluid sample is detected without passing through the microcolumnar wall. The fluid sample can flow from an inlet end to an outlet end of the microcolumn. The light source is adapted to direct a light of a suitable wavelength to cause a desired light interaction with the fluid sample. As a result of the light interaction, light radiates from the fluid sample in the microcolumn. The optical fiber, which has a light-inlet end nonfixedly coupled to the outlet end of the microcolumn, collects this light to gather information on the presence or quantity of one or more analytes in the fluid sample. The analytical apparatus can further include a microcolumnar device and a detector. The microcolumnar device can include (or can be coupled to) the microcolumn of the aforementioned signal collection system. Likewise, the detector can include (or can be coupled to) the aforementioned optical fiber.

A method for analyzing a fluid sample and a method of making the analytical apparatus for analyzing a fluid sample are also provided in the present invention.

In the present invention, the interfacing end of the microcolumn and the interfacing end of the optical fiber are nonfixedly coupled together. Examples of structures for nonfixed coupling include a flare at the interfacing end of the microcolumn to confine the interfacing end of the optical fiber and a channel to confine the interfacing end portions of the microcolumn and the optical fiber. With such nonfixed coupling structures, the axial detection (i.e., detecting light that travels generally in a direction of the axis of the microcolumn) of a light interaction can be easily implemented. For this reason, the analytical apparatus of the present invention can be advantageously employed to analyze fluid samples efficiently.

In the prior art, detection of a light interaction (such as fluorescence) in a capillary is generally through the capillary wall and the detector faces the capillary axis at an angle (acute or right angle, e.g., as described in U.S. Pat. Nos. 4,675,300 and 5,006,210). Light from the fluid sample has to travel from the capillary through air into a detector which may have lens or optical fibers. Due to the large difference in refractive indices between air and such lens or optical fibers, some of the light is reflected from the detector. As a result, less light is collected by the detector. In instances where the incident light also has to pass through air into a capillary, light is scattered by the wall of the capillary. In the present invention, light radiating from the fluid sample does not have to pass through the micro columnar wall and air. Thus, more of the desired radiation can be collected. Furthermore, since signal light is collected by optical fiber (s), less scattered light is collected than in prior art methods.

The immersion of the interfacing ends of the microcolumn and the optical fiber in a flushing fluid can also further reduce scattered light by the microcolumnar wall.

The prior art method of directing the incident light at an acute angle (and detecting light interaction also at an acute angle) necessitates the microcolumn, the detector, and the light source to each point at a different direction. The result is a bulky apparatus. In contrast, in the present invention, the microcolumn and the optical fiber are aligned. Further, they are flexible. Therefore, a more compact apparatus can be constructed.

Because of the capability to easily align the microcolumn with the optical fiber, the present invention is well-suited for situations wherein frequent coupling and decoupling of the microcolumn and detector is needed. For example, in one embodiment, the curved or angular shape of the inwardly facing (or lumenal) wall of a channel naturally guides the flexible microcolumn and the optical fiber interfacing end portions to align in a substantially collinear fashion without radial (i.e., lateral) adjustment by an operator (i.e., the microcolumn and the optical fiber self-align radially or laterally). This greatly simplifies the aligning process. Further, because the positions where the microcolumn and the optical fiber are mechanically affixed to the channel are not important, the microcolumn and the optical fiber can be sealed effectively against the channel to reduce the risk of fluid leakage. The interfacing end portions can self-aligned without depending on being attached to (i.e., they are detachable from) the channel. As a result, the microcolumn and optical fiber can easily be removed from the channel for repair or replacement.

The collection of more light for transmission towards the detector not only increases the signal, it also reduces the interference between adjacent microcolumns and optical fibers in a multimicrocolumnar system. Such a multimicrocolumnar system facilitates faster analysis and a more compact design, thereby reducing manufacturing complexity and cost. Even in a single-microcolumn system, the ease of aligning the microcolumn and the optical fiber renders the manufacturing process relatively simple.

BRIEF DESCRIPTION OF THE DRAWINGS

The following figures, which show the embodiments of the present invention, are included to better illustrate the microcolumnar analytical apparatus of the present invention. In these figures, wherein like numerals represent like features in the several views.

DETAILED DESCRIPTION OF THE INVENTION

The analytical apparatus of the present invention can be used to detect light that radiates from inside a microcolumn (or capillary) without passing through the wall of the microcolumn. An optical fiber is positioned close to the outlet (i.e., exit) end of the microcolumn to receive from it the radiated light. The light-inlet end of the optical fiber and the outlet end of the microcolumn are nonfixedly coupled together. As used herein, "nonfixedly coupling" between an end of a microcolumn and an end of an optical fiber refers to the positioning and maintaining the position of these ends relative to each other in close proximity without rigidly affixing any of these ends to any mechanical structure.

Figure 1:
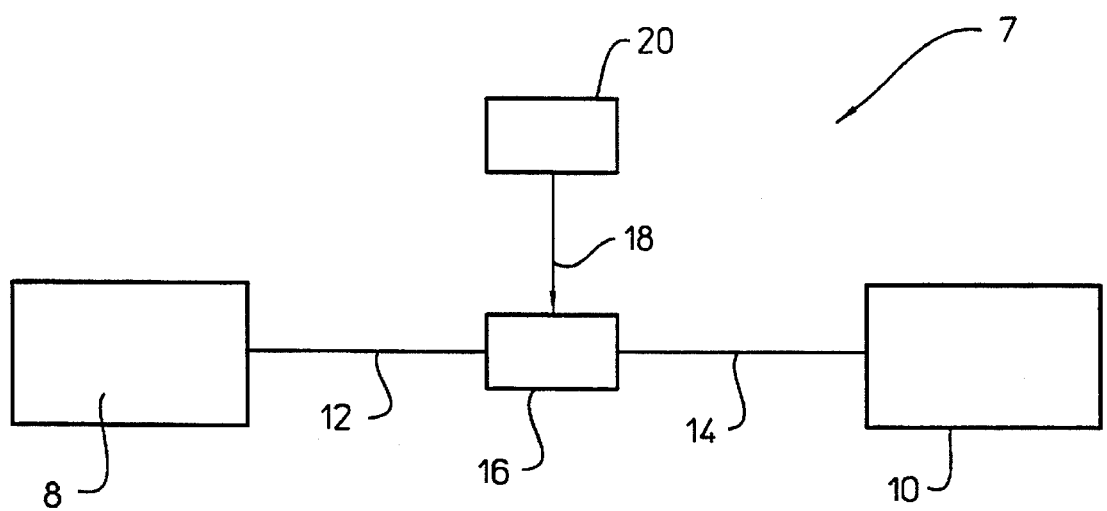
FIG. 1 shows a schematic representation of a microcolumnar analytical apparatus according to the present invention.

FIG. 1 shows a schematic representation of the analytical apparatus of the present invention. In FIG. 1, the microcolumnar analytical apparatus 7 has a microcolumnar device 8 (preferably a microcolumnar device for the separation of analytes, e.g., LC or CE) and a fiber-optics detector 10. The microcolumnar device 8 has a microcolumn (or capillary) 12 that interfaces with an optical fiber 14 in a detecting region 16 at which light (e.g., a light beam 18) from a light source 20 can be directed.

Embodiments of the Analytical System

Figure 2:
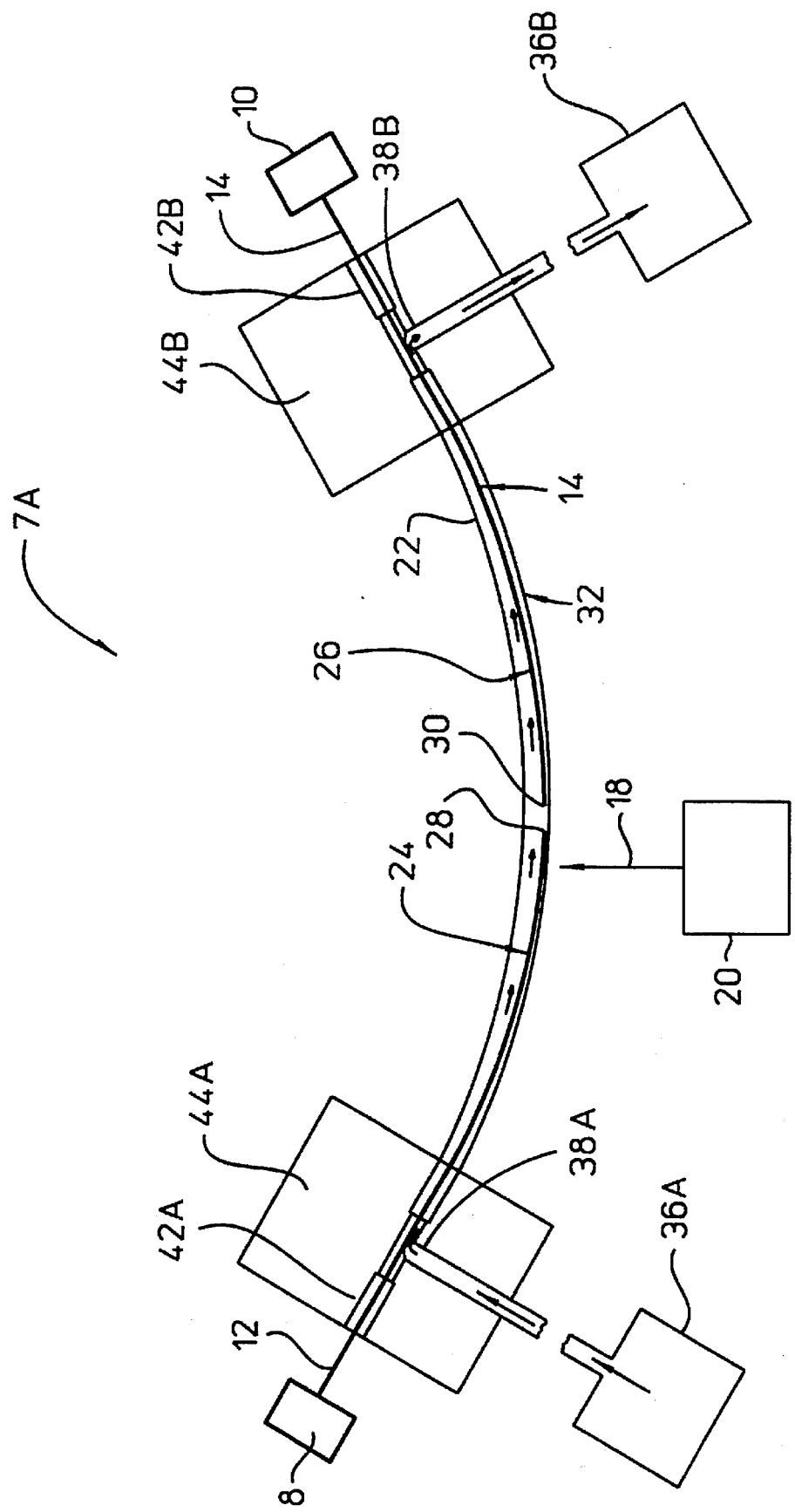
FIG. 2 shows a schematic view of an embodiment of the microcolumnar analytical apparatus according to the present invention, showing more details than in FIG. 1.

FIG. 2 shows (not to scale) an embodiment of an analytical system of the present invention. A channel 22 conducts a flow of a flushing fluid (the direction of which is shown by arrows in the channel). A microcolumn 12 having a lumen (not shown in FIG. 3, but shown as 13 in FIG. 3) and an end portion 24 with an end 28 extends from a microcolumnar separation device 8 (such as a liquid chromatograph (LC) or a capillary electrophoresis (CE) apparatus) into the channel 22. As used herein, the term "microcolumn" includes conduits with a small lumen, columns in liquid chromatography (LC), capillaries in capillary electrophoresis (CE), and the like (as long as the conduit can permit a fluid flow). Facing the microcolumn 12 is an optical fiber 14 that extends from a detector 10. The channel 22 encircles (or encloses) an end portion 24 of the microcolumn 12 and an end portion 26 of the optical fiber 14. The interfacing end 28 (i.e. the end that faces the optical fiber 14) of the microcolumn 12 is proximate to the interfacing end 30 (i.e., the end that faces the microcolumn 12) of the optical fiber 14 such that light radiating from inside the microcolumn out the interfacing end 28 can be substantially received (or sensed) by the interfacing end 30 of the optical fiber 14. A light source 20 (preferably a laser that emits a light of a suitable wavelength to cause the desired light interaction in a fluid sample in the microcolumn) is positioned such that it can direct a light beam 18 to a location 34 (shown in FIG. 3) of the microcolumn near the interfacing end 28. This light beam 18 penetrates the microcolumnar wall 35 and irradiates the fluid sample 19 (shown in FIG. 3) in the microcolumn.

Because the microcolumn 12 and the optical fiber 14 are relatively small and long, they are somewhat flexible. However, the selected materials of construction of the microcolumn and the optical fiber render an elasticity to the microcolumn and the optical fiber so that they tend (i.e., have a reacting force) to return to their original shape when they are flexed. The channel 22 is bent so that it has a nonlinear (i.e., not straight) portion 32. In the embodiment shown in FIG. 2, the channel 22 is a tube having a generally circular cross section.

Figure 3:
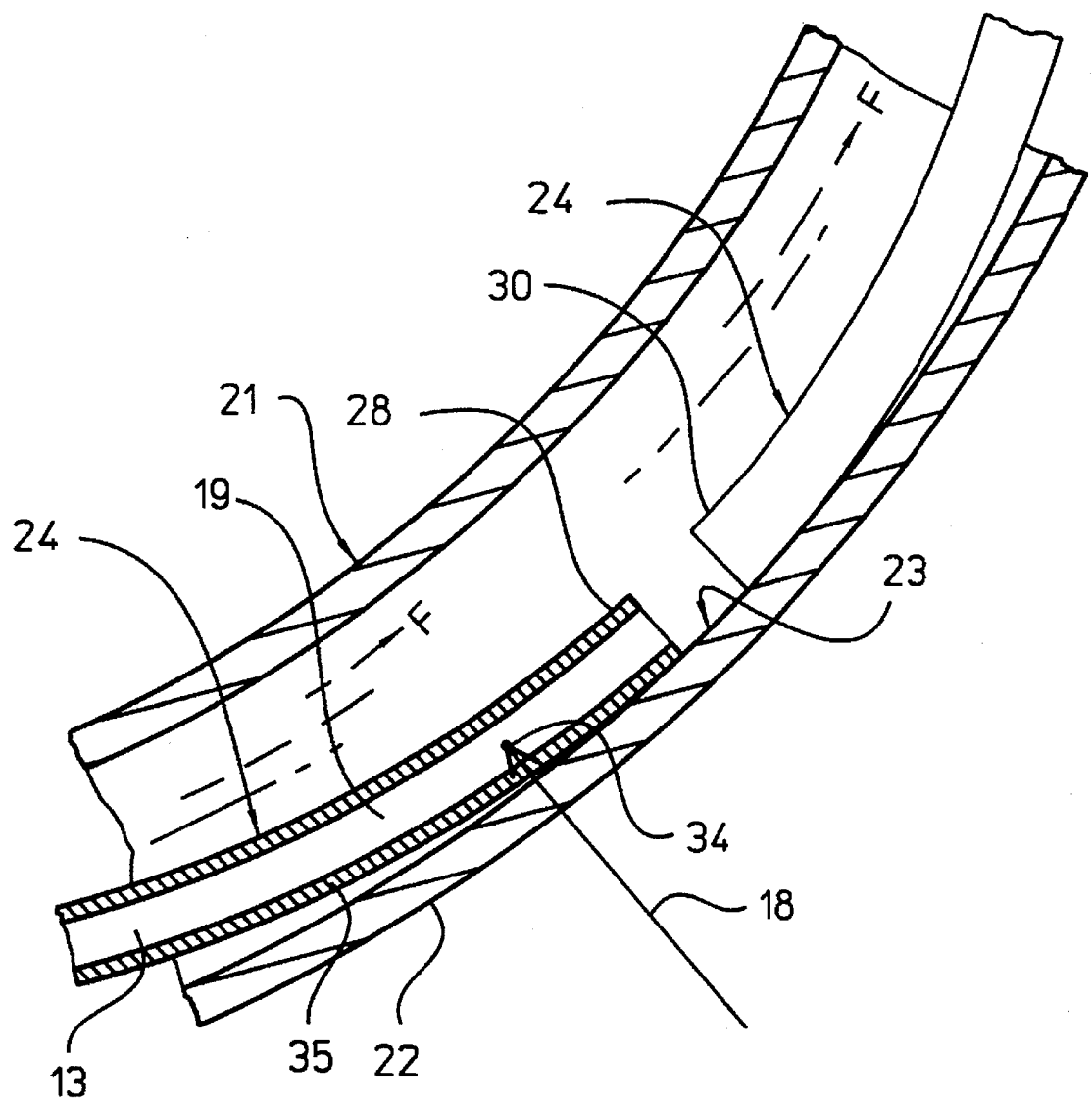
FIG. 3 is a sectional view of the interfacing region of the microcolumnar analytical apparatus of FIG. 2 in portion.

FIG. 3 shows the detecting (or interfacing) region 16 of an analytical apparatus 7A (not showing the light source) of the present invention. The flexible nature of the microcolumn 12 and optical fiber 14 enables them to flex without breaking. Thus, the curvature of the bent portion 32 of the channel 22 causes the inwardly facing wall 23 (lumenal wall) of the channel to press on the outside walls of the microcolumn and the optical fiber interfacing end portions 24, 26 to constrain (or confine) them from radial movement (i.e., in a direction perpendicular to the centerline of the channel) at the points of contact. The centerline of a tubular channel having a circular cross section is the tubular axis. Similarly, the centerline of a tubular microcolumn having a circular cross section or of a cylindrical optical fiber is its axis. In this way, the outlet end (or exit end) 28 of the microcolumn 12 is proximate to the light-inlet end 30 (i.e., the end through which the light radiated from the microcolumn enters) of the optical fiber 14. The distance between these two interfacing ends 28, 30 is preferably small enough to prevent excessive loss of light around the interfacing end 30 of the optical fiber yet large enough to not hinder fluid from exiting the microcolumn. For example, this distance (i.e., the gap) can be from about 0.2 to 0.5 of the outside diameter of the smaller of the microcolumn 12 and the optical fiber 14.

In the embodiment shown in FIG. 2 and FIG. 3, due to its circular cross-sectional internal curvature, the channel (i.e., its lumenal wall) constrains the lateral movement of the interfacing ends 28 and 30 of the microcolumn 12 and the optical fiber 14, respectively. As a result, these interfacing ends 28 and 30 are conveniently aligned. As used herein, the term "interfacing end portion" refers to the portion of the microcolumn or the optical fiber including the corresponding interfacing end. Because the interfacing end portions of the microcolumn and the optical fiber are not attached (or rigidly affixed) to any structure, if desired (e.g., to repair the microcolumn or the optical fiber), the microcolumn or the optical fiber can be slid out of the channel and later slid back in again without loss of alignment. The interfacing ends 28, 30 will slide back (against the channel lumenal wall) into alignment if they are moved laterally and released. Thus, the channel can be considered to "slidably confine" the interfacing ends and end portions of the microcolumn and the optical fiber.

As previously stated, the interfacing end portions of the microcolumn and the optical fiber are aligned, i.e., their centerlines are generally collinear and the ends 28, 30 are proximate to each other. As used in herein, the term "collinear" when referring to interfacing end portions of the microcolumn and optical fiber means the extrapolation of the centerline of the interfacing end portion of a microcolumn coincides generally with the centerline of the interfacing end portion of an optical fiber. Preferably, the microcolumn 12 and the optical fiber 14 have about the same outside diameter so that their interfacing ends 28 and 30, when resting against the lumenal wall of the channel 22, are proximate to and face each other to achieve the best signal light reception with little or no disturbance of the exiting liquid flow from the microcolumn. Because the cross section of the channel has an arcuate (e.g., round) or angled (e.g. polygonal, as will be described later) perimeter and the interfacing end portions 28, 30 of the microcolumn and the optical fiber are not fixedly attached to (i.e., they are detachable from) the channel, the channel continues to keep the interfacing end portions 28, 30 in alignment even if they are moved (as in a microcolumn or optical fiber being taken out for repair). This greatly simplifies the process of coupling the interfacing ends for optimal light detection.

As shown in FIG. 2, the channel 22 is connected to a reservoir 36A containing a flushing fluid. The chemical and physical characteristics of the flushing fluid is selected based on the nature of the microcolumnar apparatus. For example, it can be water if it is simply used for flushing away a fluid sample in LC. It can also be an electrically-conductive buffer having ions if it is used for flushing a CE fluid sample. The microcolumn 12 is connected to its microcolumnar device (e.g., a capillary electrophoresis apparatus). A fluid-conducting connecting piece 38A (e.g., a T-shaped piece as shown in FIG. 2) can be used to connect functionally the channel 22 to the reservoir 36A and to allow the microcolumn 12 to pass therethrough. A seal (such as a polymeric sleeve) 42A can be used to encircle the microcolumn to seal against the fluid-conducting connecting piece 38A to prevent fluid leakage. The reservoir 36, the channel 22, and the seal 42A can be secured to a support 44A to prevent any undesired movement. Likewise, another fluid-conducting connecting piece 38B, reservoir 36B, seal 42B, and support 44B can be associated with the optical fiber 14 in an analogous fashion.

It is to be understood that structures other than T-shaped fluid-conducting connecting pieces can be used for connecting the channel to the reservoirs. For example, the channel 22 can be directly connected to a reservoir and the microcolumn and the optical fiber can extend through the wall of the channel. The elasticity of the channel wall, especially if the channel is made with polymeric material, can adequately seal around the microcolumn and the optical fiber to prevent excessive fluid leakage.

For a capillary electrophoresis (CE) system, one electrode can be a fitting that is connected to the channel 22. For example, in FIG. 2, the T-shaped piece 38A can be made of a suitable metal to provide one electrode (e.g., ground potential) for the CE system. When an electricity-conducting flushing fluid is used, by providing another electrode connected to the inlet end of the CE system, a suitable DC voltage can be applied across the two ends of the CE capillary (i.e., microcolumn).

Although, because of its simplicity of construction, a continuous, arcuate tube is preferred for the bent portion 32 of the channel 22, channels of other shapes can also be used as long as they can be made in such a way to assist the microcolumn and the optical fiber to align with each other in a substantially collinear fashion. A straight channel can also be used as long as the interfacing ends can be aligned proximate to each other. For example, the interfacing portion of the channel 22 (i.e., the mid portion of the channel which encloses the interfacing end portions 24, 26 of the microcolumn 12 and the optical fiber 14) can be shaped so that it is substantially straight whereas the portions more remote from the interfacing ends are arcuate. The straight portion of such a bent channel can enable longer portions of the microcolumn and the optical fiber at the interfacing region to contact the inwardly facing wall of the channel. This configuration has the advantage of allowing the interfacing end portions 24, 26 to align with each other in an essentially straight fashion.

If the microcolumn and the optical fiber have different outside diameters, a sleeve can be put on the smaller one to approximate the outside diameter of the larger one. In this way, the interfacing ends can be better aligned.

Figure 4:
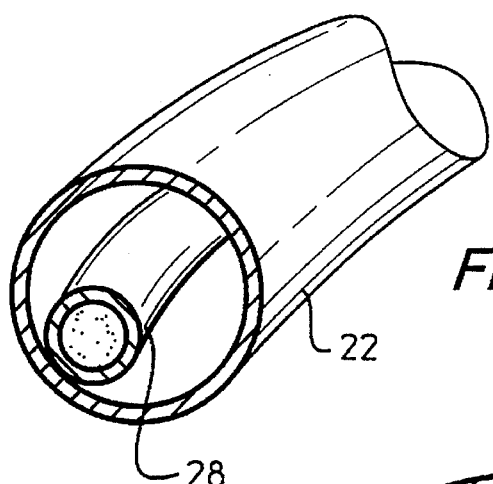
FIG. 4 is an isometric view of a portion of the interfacing region of an embodiment of the microcolumnar analytical apparatus showing a channel with a circular cross-section at the interfacing end of a microcolumn.
Figure 5:
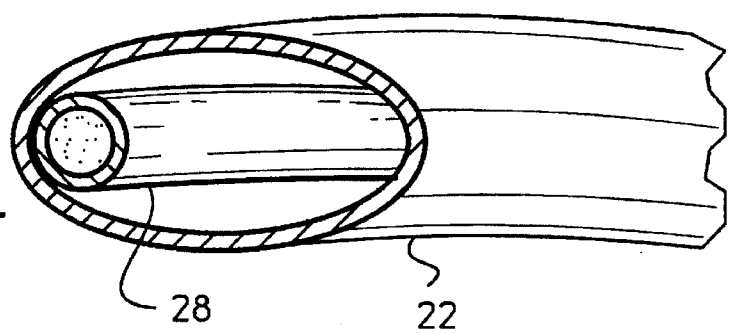
FIG. 5 is an isometric view of a portion of the interfacing region of an embodiment of the microcolumnar analytical apparatus showing a channel with an oval cross-section at the interfacing end of a microcolumn.
Figure 6:
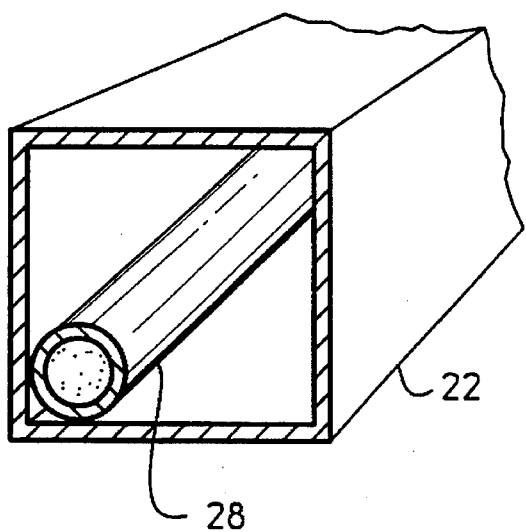
FIG. 6 is an isometric view of a portion of the interfacing region of an embodiment of the microcolumnar analytical apparatus showing a channel with a square cross-section at the interfacing end of a microcolumn.
Figure 7:
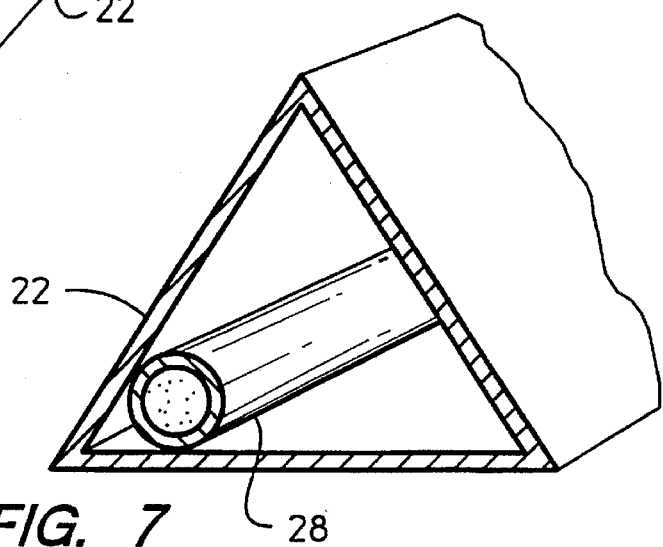
FIG. 7 is an isometric view of a portion of the interfacing region of an embodiment of the microcolumnar analytical apparatus showing a channel with a triangular cross-section at the interfacing end of a microcolumn.

A preferred embodiment of the microcolumnar analytical apparatus having a tubular channel with a circular cross-section (as shown in FIG. 4) has been described. However, channels having various cross-sectional shapes can be also used—for example, channels with a oval cross-section (FIG. 5), square cross-section (FIG. 6), triangular cross-section (FIG. 7), rectangular cross-section, other polygonal cross-sections, and the like. In channels with flat inwardly-facing walls e.g., a channel with a square cross section), two adjacent walls connect to form a groove for guiding the position of the interfacing end portions of the microcolumn and the optical fiber.

The channel can be made with a relatively rigid material that enables the channel to maintain a bent shape. Suitable materials include, but are not limited to, silicon-based materials (such as glass), polymers (such as polytetrafluoroethylene, polyethylene), and the like, that admit incident light of selected wavelengths to cause light interaction. In an embodiment wherein the incident light can irradiate the microcolumn without passing through the channel wall, the channel can be made of a nontransparent material such as a metal. An example is a channel that has an opening in the channel wall for an optical fiber to penetrate therethrough to irradiate the microcolumn in the channel. Preferably, at least a portion of the channel is transparent (or translucent) to visible light, so that the positions of the interfacing ends of the microcolumnar sections can be determined from outside the channel.

The microcolumnar interfacing end portion 24 can be part of the microcolumn of the microcolumnar device 8 or it can be a discrete section connected to the microcolumn of the microcolumnar device by a coupling sleeve or fitting (which can be a polymeric material, e.g., polytetrafluoroethylene, TEFLON). Likewise, the interfacing end portion 26 of the optical fiber can be either a discrete section or the optical fiber of the detector 10.

Figure 8:
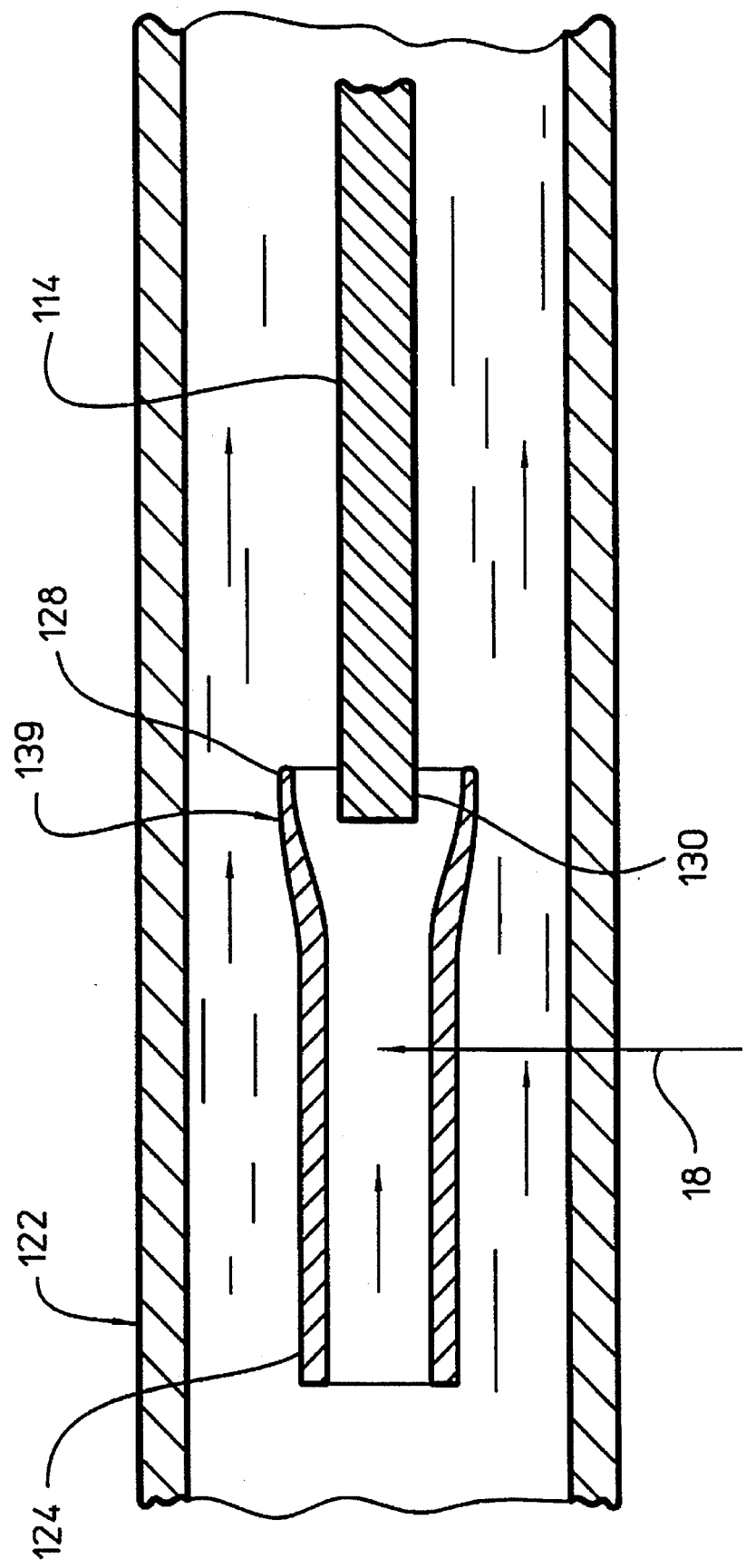
FIG. 8 is a sectional view of another embodiment of the interfacing region of a microcolumnar analytical apparatus in portion showing a flare according to the present invention.

FIG. 8 shows a portion of another embodiment of the analytical apparatus of the present invention. In this embodiment, the microcolumnar interfacing end portion 124 has a flare (or enlarged portion) 139 at the interfacing end 128. This flare 139 has an enlarged opening to the lumen of the microcolumn for receiving the interfacing end 130 of the optical fiber 114, thereby facilitating the alignment and nonfixed confinement of the interfacing end 130 of the optical fiber to the interfacing end 128 of the microcolumn. In this embodiment, the channel 122 need not have an arcuate portion, although such an arcuate portion is preferred to reduce any lateral (i.e., generally perpendicular to the centerline of the microcolumn and the optical fiber) movement of the interfacing ends 128, 130. A light beam 18 can be directed perpendicularly to the microcolumnar interfacing end portion 124. The channel 122 is oriented such that the flushing fluid flows generally parallel to the interfacing end portions 124, 126.

Figure 9:
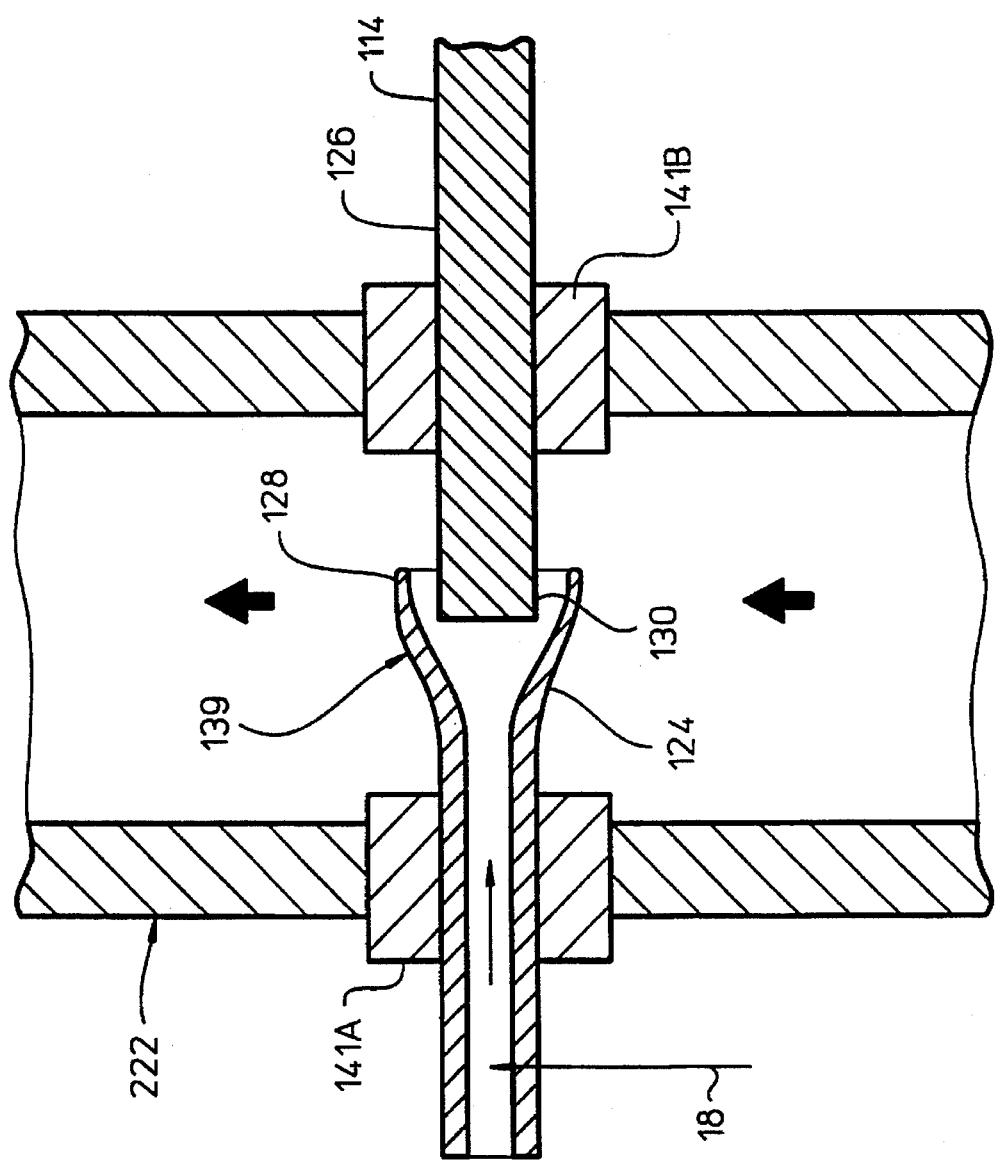
FIG. 9 is a sectional view of yet another embodiment of the interfacing region of a microcolumnar analytical apparatus in portion showing a flare according to the present invention.

FIG. 9 shows a portion of yet another embodiment of the analytical apparatus in which the microcolumnar interfacing end portion 124 has a flare 139 at the interfacing end 128 for nonfixed coupling to the interfacing end 130 of the optical fiber 114. In this embodiment, the channel 222 is arranged such that the flushing fluid flows in a direction generally perpendicular to the centerlines of the interfacing end portions 124, 126 of the microcolumn and the optical fiber. To prevent leakage of the flushing fluid, sleeves 141A, 141B can be used to fit around the interfacing end portions 124, 126, respectively, to seal against the wall of the channel 222.

Figure 10:
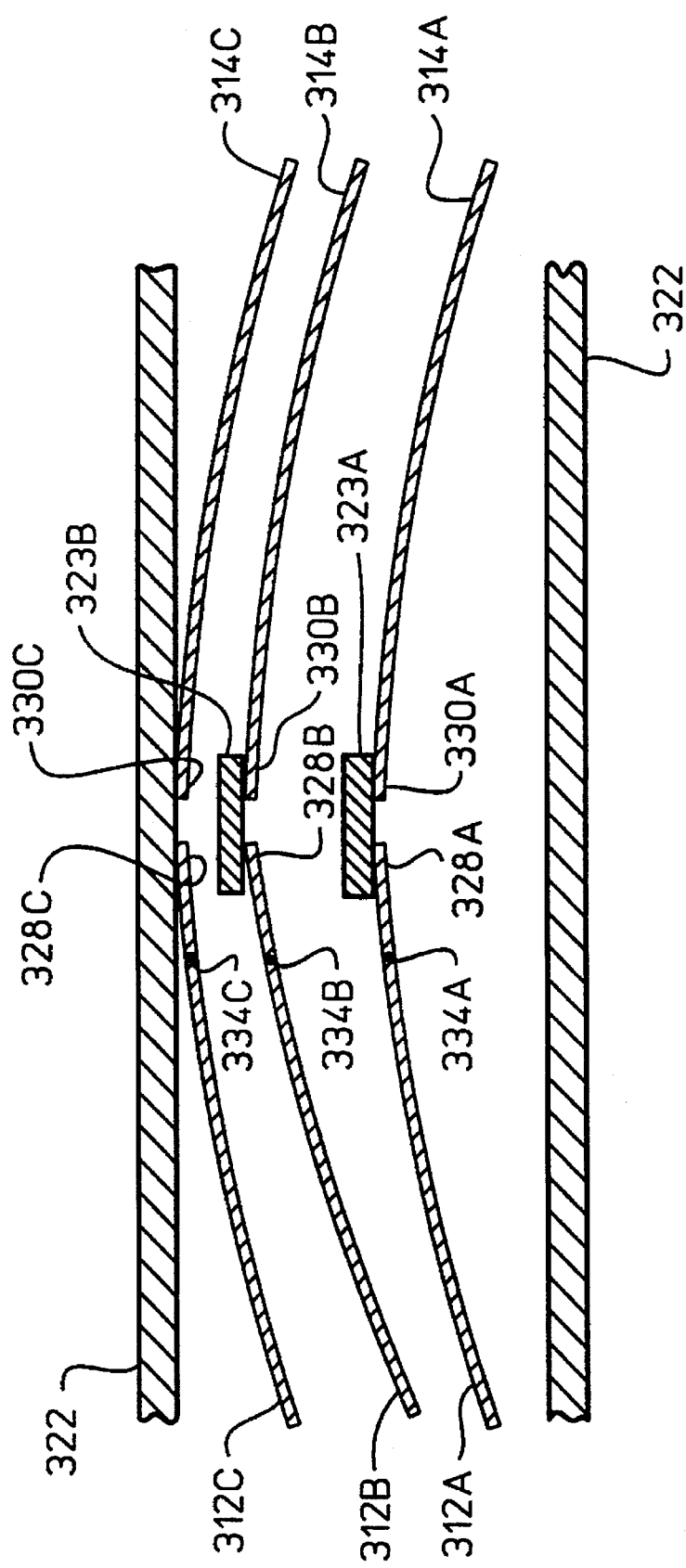
FIG. 10 is a sectional view of another embodiment of the interfacing region of a microcolumnar analytical apparatus in portion showing multiple microcolumns and multiple optical fibers according to the present invention

FIG. 10 shows a portion of an embodiment of the analytical apparatus that has multiple (two or more) microcolumns and multiple optical fibers. The channel 322 has projections 323A, 323B to act as guides so that each microcolumn can be aligned with a corresponding optical fiber. The interfacing ends 328A, 328B, 328C of the microcolumns 312A, 312B, 312C and the interfacing ends 330A, 330B, 330C of the optical fibers 314A, 413B, 314C rest against the projections 323A, 323B and the wall of the channel 322, respectively, due to the resilient flexibility of their corresponding interfacing end portions. In this embodiment, light beams (going into the plane of the paper in FIG. 10 and not shown) are directed (or focused) to fluid samples at locations 334A, 334B, 334C on microcolumnar interfacing end portions 312A, 312B, 312C, respectively. However, it is understood that the light beams can also impinge on the microcolumns at a non-perpendicular angle. Alternatively, the microcolumns can be arranged generally in a plane and a light beam can be directed to the fluid samples in a path generally parallel to that plane and in such a way so that one microcolumn is preferably not shielding another microcolumn from the incident light.

Although such multiple-microcolumn systems can be implemented in a tubular channel, such a configuration is particularly suitable if the channel is an open-top channel sealable with a cover (e.g., with a flat bottom so that guides, such as projections 323A, 323B, can easily be made). An open-top channel facilitates manipulation of the interfacing end portions for alignment. It is contemplated that the guides can be features, such as grooves, ridges, hooks, and the like, that can be incorporated in the channel, whether the channel has an open top or not. Preferably, the microcolumns and optical fibers are separated far enough or the guides shield them adequately so that light radiating from the fluid sample in one microcolumn will not substantially transmit to an optical fiber coupled to another microcolumn.

In the present invention, because the light-inlet end of an optical fiber is positioned proximate to and aligned with the outlet end of a corresponding microcolumn, very little light scattered by the microcolumn is collected by the optical fiber. For the same reason, the cross-talk between microcolumns in a multiple-microcolumn apparatus is also minimized. Thus, the present light detecting method is advantageous over a method of detecting light interaction through a microcolumnar wall using a detector at an angle to the centerline of the microcolumn (as in the prior art methods).

The Microcolumnar Device

The microcolumnar device 8 interfaced with the detector 10 in the present invention can be any means by which a fluid is conducted through a microcolumn. In fact, as long as the microcolumn contains a fluid sample at which light can be directed for light interaction, that microcolumn need not perform any separation function but may merely transfer fluid as a conduit. Preferably, the microcolumn performs a function of separating analytes in a fluid sample, such as a liquid in liquid chromatography (LC) or capillary electrophoresis (CE), e.g., capillary zone electrophoresis (CZE).

A particularly useful type of liquid chromatograph suitable for the present invention is high performance liquid chromatograph (HPLC). However, any microcolumnar separation device that utilizes an analytical microcolumn for separating different analytes in a fluid sample can also be used. Examples of chromatography techniques practicable for such a microcolumnar separation include reverse phase chromatography, size exclusion chromatography, adsorption chromatography, affinity chromatography, ion exchange chromatography, and the like. Liquid chromatography and high performance liquid chromatography, as well as the equipment for such techniques are generally known in art.

The separation of analytes by the microcolumn can be based on the physical and chemical nature of the analytes, as well as on the physical and chemical characteristics of the microcolumn (such as packing, charge, and the like), which affect the analytes' speed of passage through the microcolumn. The dimensions of the microcolumn are dependent on the separation technique selected and the resolution desired. Thus, the length, inside diameter (i.d.), and outside diameter (o.d.) of the microcolumn are dependent on the technique of separation and the resolution desired. For LC, although microcolumns of other sizes can be used, the microcolumn has a typical inside diameter (i.d.) of about 10 μm to about 5000 μm, preferably about 100 μm to about 2000 μm. The o.d. of the microcolumn is generally selected such that the microcolumn has the mechanical strength and integrity to allow operation with the appropriate pressure and the necessary manipulation. For example, the o.d. of a microcolumn for HPLC is typically about 400 μm to about 10 mm.

Likewise, for CE, although microcolumns of other sizes can be used, generally, the inside diameter (i.d.) of the CE microcolumn is 5 μm to about 200 μm. The thickness of the column is such that the column will have the mechanical integrity and strength for operation under the pressure and appropriate for manipulation for capillary electrophoresis. Techniques of selecting the dimensions (including length, i.d., o.d.) and the voltage for the separation of particular types of analytes (e.g., nucleic acids) in a fluid sample by capillary electrophoresis are well known in the art.

The material of construction of the microcolumn is dependent on the type of analytical technique used. The selection of the material is affected by the pressure exerted in the microcolumn and the chemical resistance desired. Commonly available microcolumns for LC can be made of metal (e.g., stainless steel), nonmetallic inorganic material (e.g., fused silica), as well as a polymer such as polytetrafluoroethylene (PTFE), polyether ether ketone (PEEK), and the like. Nonmetallic capillaries are generally used in CE. The selection of the dimensions and the material of construction of the microcolumns for separation means such as liquid chromatography and capillary electrophoresis are known in the art. In a microcolumnar device in which the microcolumn does not transmit light of the desired wavelength, the microcolumn can be coupled to another microcolumn (which transmits such light) to transfer a fluid sample thereto for irradiation to cause a light interaction.

Operation of the Apparatus

Generally, the microcolumnar device is operated under standard procedures to elute the analytes. For example, a fluid sample containing target analytes is sent through the microcolumnar device to separate the target analytes in the microcolumn (e.g., in LC or CE). Methods and devices for producing and directing a suitable beam of light to cause light interaction are known in the art and can be adapted for use in the present invention. For example, lasers and focusing mechanisms of U.S. Pat. Nos. 4,675,300 or 5,006,210 can be used. Also, the method of using optical fibers for focusing light to a fluid sample as described by U.S. Pat. No. 5,324,401 can be adapted for the present invention, especially for multiple microcolumn irradiation. However, in the present invention, the irradiation of fluid samples are preferably at an angle (more preferably a right angle) to the microcolumn rather than axially into the microcolumn. An incident light beam is directed to the microcolumn (e.g., at the centerline thereof) proximate the interfacing end at an angle generally perpendicular to the centerline of the microcolumn. In this way, before an analyte exits the microcolumnar interfacing end, it is exposed to the incident light, which causes a light interaction, such as fluorescence, indirect fluorescence, phosphorescence, Raman scattering, and the like. As a result of the light interaction, light radiates from the analyte (or from other substances in the fluid sample) and exits the microcolumnar interfacing end (e.g., end 28 in FIG. 2).

The interfacing end (e.g. end 30) of the optical fiber receives and conducts light from the light interaction to the other part of the detector (e.g., photomultiplier, electronics, etc.). The detector can include a photomultiplier, charge-coupled device (CCD), and the like. The optical fiber can be any optical fiber (e.g., made of fused silica, polymeric material, and the like) capable of receiving and conducting the desired light radiating from the analyte (or fluid sample) as a result of the light interaction. Such optical fibers and light detectors are known in the art. The interfacing end of the optical fiber is large enough to receive adequate light from the microcolumn to permit effective analysis of the target analytes. Preferably, the core of the optical fiber is not so larger that it collects an excessive amount of scattered light. The flushing fluid continuously flushes the fluid sample exiting the microcolumn 12 away from the illuminating path of the incident light beam 18 so that any fluid sample external to the microcolumn will not interfere with the analysis. The gap between the interfacing ends of the microcolumn and the optical fiber is preferably occupied by the flushing fluid.

Although the illustrative embodiments of the analytical system and the method of using the system of the present invention have been described in detail, it is to be understood that the above-described embodiments can be modified by one skilled in the art, especially in sizes and shapes and combination of various described features without departing from the spirit and scope of the invention. For example, channels of different shapes can also be used. Also, the interfacing end of the optical fiber can be inserted into the microcolumn. A flare at the interfacing end of the microcolumn can be used to facilitate such an insertion.

What is claimed is:

1. An analytical system for analyzing a fluid sample, comprising:

(a) microcolumn for conducting the fluid sample therethrough, the microcolumn having an axis, a microcolumnar wall, an inlet end, and an outlet end, the fluid sample flowing from the inlet end to the outlet end;

(b) light source for delivering light through the microcolumnar wall into the microcolumn proximate the outlet end thereof, the light being of a wavelength to cause light interaction with the fluid sample to result in light being radiated from the fluid sample in the microcolumn; and (c) detectional optical fiber having a light-inlet end non-fixedly coupled to the outlet end of the microcolumn by resilient flexibility of said optical fiber and said microcolumn causing an end portion of said optical fiber containing said light-inlet end and an end portion of said microcolumn containing said outlet end to resist against a guide such that said light-inlet end of the optical fiber is proximate to said outlet end of said microcolumn for detecting light that is radiated from the fluid sample without passing through the microcolumnar wall, the light resulting from the light interaction providing information on the presence or quantity of an analyte in the fluid sample.

2. The system according to claim 1 wherein the microcolumn is an analytical microcolumn effective for separating an analyte from another analyte.

3. The system according to claim 1 further comprising a detector such that the optical fiber nonfixedly coupled to the microcolumn is an optical fiber of the detector.

4. The system according to claim 1 further comprising a microcolumnar separation device and a detector such that the microcolumn nonfixedly coupled to the optical fiber is a microcolumn in the microcolumnar separation device and such that the optical fiber nonfixedly coupled to the microcolumn is an optical fiber of the detector.

5. The system according to claim 1 wherein the light source is a laser capable of emitting light having a wavelength in the range of 200 nm to 1500 nm and is adapted to deliver light generally perpendicular to the axis of the microcolumn proximate to the outlet end of the microcolumn.

6. The system according to claim 1 wherein said guide couples only one detectional optical fiber per microcolumn and neither the light-inlet end of the optical fiber nor the outlet end of the microcolumn are fixedly attached to the guide, and the optical fiber does not contact the lumen of the microcolumn.

7. An analytical system for analyzing a fluid sample, comprising:
(a) microcolumn for conducting the fluid sample therethrough, the microcolumn having an axis, a microcolumnar wall, an inlet end, and an outlet end, the fluid sample flowing from the inlet end to the outlet end;
(b) light source for delivering light through the microcolumnar wall into the microcolumn proximate the outlet end thereof, the light being of a wavelength to cause light interaction with the fluid sample to result in light being radiated from the fluid sample in the microcolumn;
(c) optical fiber having a light-inlet end nonfixedly coupled to the outlet end of the microcolumnar for detecting light that is radiated from the fluid sample without passing through the microcolumnar wall, the light resulting from the light interaction providing information on the presence or quantity of an analyte in the fluid sample; and
(d) a channel having an inwardly facing wall and a centerline, the channel enclosing at least an end portion of the microcolumn having the outlet end and at least an end portion of the optical fiber having the light-inlet end, wherein a flushing fluid can flow past the outlet end of the microcolumn to flush the fluid sample exiting the microcolumn from the light-inlet end of the optical fiber.

8. The system according to claim 7 wherein said end portions are constrained by the inwardly facing wall to self align such that the outlet end of the microcolumn is proximate to the light-inlet end of the optical fiber to facilitate light radiating from the fluid sample to be received by and transmitted through the optical fiber.

9. The system according to claim 7 wherein the channel has at least one bent portion to nonfixedly constrain the end portion of the microcolumn and the end portion of the optical fiber.

10. The system according to claim 7 wherein the system includes at least two microcolumn-optical-fiber pairs each comprising a microcolumn nonfixedly coupled to an optical fiber, and wherein the system further includes a guide means for constraining and aligning a microcolumn to an optical fiber to nonfixedly couple them in at least one of the microcolumn-optical-fiber pairs.

11. The system according to claim 7 wherein the channel has one or more arcuate portions such that the curvature of the one or more arcuate portions and the elasticity of the microcolumn and of the optical fiber cause the wall of the one or more arcuate portions to press on the microcolumn and on the optical fiber to align them such that said end portions are generally collinear.

12. The system according to claim 7 wherein the channel is arranged in relation to the microcolumn and the optical fiber such that flushing fluid flows in a direction perpendicular to the axis of the microcolumn.

13. The system according to claim 7 wherein the channel is arranged with the microcolumn and the optical fiber such that flushing fluid flows in a direction parallel to the axis of the microcolumn.

14. An analytical system for analyzing a fluid sample, comprising:
(a) microcolumnar device having microcolumn for separating analytes, the microcolumn having an axis, a microcolumnar wall, an inlet end, and an outlet end such that the fluid sample can flow from the inlet end to the outlet end;
(b) light source for delivering light through the microcolumnar wall into the microcolumn proximate the outlet end thereof, the light being of a wavelength to cause light interaction with the fluid sample in the microcolumn to result in light being radiated therefrom; and
(c) detector including an optical fiber having a light-inlet end nonfixedly coupled to the outlet end of the microcolumn for detecting light that is radiated from the fluid sample without passing through the microcolumnar wall, said optical fiber having an end portion containing said light-inlet end by resilient flexibility to rest against a guide to maintain position proximate to said outlet end of said microcolumn.

15. A method for analyzing a fluid sample, comprising:
(a) introducing the fluid sample into a microcolumn to move the fluid sample to an outlet end of the microcolumn;
(b) irradiating the fluid sample to cause a light interaction with the fluid sample in the microcolumn proximate to the outlet end thereof, the light interaction causing light to radiate from the fluid sample;
(c) detecting light radiated from the fluid sample without passing through the microcolumnar wall with an optical fiber having a light-inlet end nonfixedly coupled to the outlet end of the microcolumn, said radiated light from the fluid sample resulting from the light interaction providing information on the presence or quantity of an analyte in the fluid sample; and
(d) nonfixedly coupling said light-inlet end of the optical fiber with said outlet end of the microcolumn using a channel having an inwardly facing wall and a centerline to encircle at least an end portion of the microcolumn having the outlet end and at least an end portion of the optical fiber having the light-inlet end, wherein a flushing fluid can flow past the outlet end of the microcolumn to flush the fluid sample exiting the microcolumn from the light-inlet end of the optical fiber.

16. The method according to claim 15 wherein said end portions are constrained by the inwardly facing wall to self align such that the outlet end of the microcolumn is proximate the light-inlet end of the optical fiber to facilitate light radiating from the fluid sample generally axially in the microcolumn to impinge on the light-inlet end of the optical fiber.

17. A method of making an analytical system for analyzing a fluid sample, comprising:

(a) providing a microcolumn for conducting the fluid sample, the microcolumn having microcolumnar wall, an inlet end, and an outlet end, such that the fluid sample can flow from the inlet end to the outlet end;

(b) positioning a light source for delivering light through the microcolumnar wall into the microcolumn proximate the outlet end thereof, the light being of a wavelength suitable to cause light interaction with the fluid sample to result in light being radiated from the fluid sample, said radiated light providing information on the presence or quantity of an analyte in the fluid sample;

(c) coupling a detector to the microcolumn, the detector having an optical fiber with a light-inlet end, such that the light-inlet end of the optical fiber is nonfixedly coupled and aligned with the outlet end of the microcolumn to detect light that is radiated from the fluid sample without passing through the microcolumnar wall; and (d) using a channel having an inwardly facing wall and a centerline to constrain at least a portion of the microcolunm having the outlet end and encircling at least a portion of the optical fiber having the light inlet end, wherein a flushing fluid can flow past the outlet end of the microcolumn to flush the fluid sample exiting the microcolumn from the light-inlet end of the optical fiber.

18. An analytical system for analyzing a fluid sample, comprising:

(a) microcolumn for conducting the fluid sample therethrough, the microcolumn having an axis, a microcolumnar wall, an inlet end, and an outlet end having a flare to provide an enlarged opening, the fluid sample flowing from the inlet end to the outlet end;

(b) light source for delivering light through the microcolumnar wall into the microcolumn proximate the outlet end thereof, the light being of a wavelength to cause light interaction with the fluid sample to result in light being radiated from the fluid sample in the microcolumn; and (c) optical fiber having a light-inlet end nonfixedly coupled to the outlet end of the microcolumn for detecting light that is radiated from the fluid sample without passing through the microcolumnar wall, the light resulting from the light interaction providing information on the presence or quantity of an analyte in the fluid sample, wherein the flare with the enlarged opening at the outlet end of the microcolumn receives and aligns said light-inlet end of the optical fiber.

19. A method for analyzing a fluid sample, comprising:

(a) introducing the fluid sample into a microcolumn to move the fluid sample to an outlet end of the microcolumn;

(b) irradiating rite fluid sample to cause a light interaction with the fluid sample in the microcolumn proximate to the outlet end thereof, the light interaction causing light to radiate from the fluid sample; and (c) detecting light radiated from the fluid sample without passing through the microcolumnar wall with an optical fiber having a light-inlet end nonfixedly coupled to the outlet end of the microcolumn, said optical fiber having an end portion containing said light-inlet end by resilient flexibility resting against a guide which bridges between said light-inlet end of the optical fiber and said outlet end of said microcolumn to maintain position proximate to said outlet end of said microcolunm, said radiated light from the fluid sample resulting from the light interaction providing information on the presence or quantity of an analyte in the fluid sample.

20. The method according to claim 19 wherein the step of detecting light further comprises nonfixedly coupling by the microcolumn having an end portion containing said outlet end of said microcolumn by resilient flexibility resting against the guide to maintain position proximate to said light-inlet end of said optical fiber.

* * * * *